United States Patent
Collingwood et al.

(10) Patent No.: US 6,285,183 B1
(45) Date of Patent: *Sep. 4, 2001

(54) METHOD AND SYSTEM FOR MEASURING THE VOLUME LOSS OF A METAL SUBSTRATE

(75) Inventors: Michael R. Collingwood, Huntington Beach; Steven G. Keener, Trabuco Canyon, both of CA (US)

(73) Assignee: McDonnell Douglas Corporation, St. Louis, MO (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/939,560

(22) Filed: Sep. 29, 1997

Related U.S. Application Data

(60) Provisional application No. 60/027,115, filed on Sep. 30, 1996.

(51) Int. Cl.$^7$ .............................. G01N 27/82; G01R 33/12
(52) U.S. Cl. ........................... 324/202; 324/238; 324/225
(58) Field of Search ..................................... 324/238, 202, 324/219, 220, 221, 225, 227, 229, 236, 237, 239, 240, 241, 242, 243

(56) References Cited

U.S. PATENT DOCUMENTS

| | | |
|---|---|---|
| 2,572,908 | 10/1951 | Brenholdt . |
| 3,450,986 | 6/1969 | Chapman et al. . |
| 3,764,897 | 10/1973 | Greenwood . |
| 3,968,681 | 7/1976 | Cornforth et al. . |
| 4,194,149 * | 3/1980 | Holt et al. .............................. 324/220 |
| 4,271,393 | 6/1981 | Hansen et al. . |
| 4,292,588 * | 9/1981 | Smith .................................. 324/229 |
| 4,652,823 | 3/1987 | Sutton . |
| 4,727,322 | 2/1988 | Lonchampt et al. . |
| 4,755,753 | 7/1988 | Chern . |
| 4,757,259 | 7/1988 | Charpentier . |
| 4,843,319 | 6/1989 | Lara . |
| 4,843,320 | 6/1989 | Spies . |
| 4,855,677 * | 8/1989 | Clark, Jr. et al. ..................... 324/220 |
| 4,909,091 * | 3/1990 | Ellmann et al. ...................... 324/220 |
| 4,954,778 | 9/1990 | Champonnois et al. . |
| 5,028,100 | 7/1991 | Valleau et al. . |
| 5,059,903 | 10/1991 | Otaka et al. . |

(List continued on next page.)

OTHER PUBLICATIONS

Thickness and Conductivity of MetallicLayers From Pulsed Eddy–Current Measurements, Cheng–Chi Tai, James H. Rose, John C. Moulder; Review of Scientific Instruments, vol. 67, Issue 11, p. 3965 (Nov. 1996).

Primary Examiner—Walter Snow
(74) Attorney, Agent, or Firm—Alston & Bird LLP

(57) ABSTRACT

The present invention provides a method for the direct measurement and quantification of the material volume loss on the surface of a substrate and thus provides an accurate depiction of the surface profile of the surface. The method of the invention comprises inducing eddy currents in a test substrate, measuring the magnitude of the eddy current produced within the substrate at a plurality of locations on the surface of the substrate, and converting the measured eddy current magnitudes at the locations to corresponding volume losses on the test surface using the eddy current magnitude measurements of a reference substrate having defects of predetermined volume loss. Typically, the measurements of the eddy current magnitude on the test surface are converted to actual volume losses by multiplying the measured eddy current magnitude for a sector of the test substrate by the area of the sector and a calibration factor ($C_f$) representing the volume per unit area eddy current magnitude. The present invention also includes a system for measuring volume loss on the surface of a test substrate.

11 Claims, 3 Drawing Sheets

U.S. PATENT DOCUMENTS

| | | |
|---|---|---|
| 5,180,969 | 1/1993 | Kwun et al. . |
| 5,311,128 | 5/1994 | Lareau et al. . |
| 5,485,082 | 1/1996 | Wisspeintner et al. . |
| 5,491,409 | 2/1996 | Flora et al. . |
| 5,510,709 | 4/1996 | Hurley et al. . |
| 5,602,474 | 2/1997 | Morrey, Jr. . |
| 5,610,517 | 3/1997 | Ma et al. . |
| 5,744,955 * | 4/1998 | Booker .................................. 324/240 |

* cited by examiner

METHOD AND SYSTEM FOR MEASURING THE VOLUME LOSS OF A METAL SUBSTRATE

CROSS-REFERENCE TO RELATED APPLICATIONS

This application is related to copending provisional application Ser. No. 60/027,115, filed Sep. 30, 1996 and claims the benefit of the earlier filing date of this application under 35 U.S.C. §119(e).

FIELD OF THE INVENTION

This invention relates to a method for determining surface defects on metal components due to corrosion and damage. More specifically, this invention relates to a method for quantifying the volume loss caused by surface corrosion and damage by measuring the magnitude of eddy current responses on the surface of the substrate.

BACKGROUND OF THE INVENTION

Corrosion damage is a significant threat to the safe operation of both military and commercial aircraft. Failure to detect and correctly quantify corrosion damage can lead to catastrophic failure of various aircraft components. Such failures can lead to the loss of the aircraft as well as loss of lives. Corrosion damage is an even more significant problem with military aircraft due to the extreme environments in which they must operate.

The relevant art is replete with systems for determining damage to metal structures. One such system includes a thermographic system for detecting exfoliation corrosion on aircraft skins. However, this technique is limited to flat surfaces and only presents images that are visually compared with surrounding areas. Traditional impedance plane eddy current techniques are also used to evaluate corrosion loss on aircraft skins. The eddy current response from a test sample is compared to the eddy current response from a reference standard. The result is a subjective evaluation of whether or not the test sample is better or worse than the reference standard. The technique is limited by the inability to produce corrosion reference standards with quantifiable defects. As a result, assessment of corrosion damage in an aircraft metallic structure has required a good understanding of the physics involved and extensive experience of a specialist in complex and time consuming inspection techniques currently available in the industry. In other words, corrosion damage determination has been highly subjective and quality depends to a large degree upon the individual conducting the evaluation.

Conventional eddy current inspection methods are typified by U.S. Pat. No. 5,510,709 to Hurley. This patent discloses an eddy current surface inspection array probe and a method for detecting cracks and flaws in aircraft skin metal immediately surrounding rivets without requiring the removal of rivets or manual scanning. The method comprises positioning a probe concentrically around the rivet. The sense coil pairs of the probe either provide a zero reading corresponding to no cracks or defects or a non-zero reading corresponding to one or more cracks or defects in the surface. Thus, this system is used to locate only two dimensional anomalies such as cracks in the surface around the rivet. Furthermore, the method described in this patent does not provide a quantified measurement of the metal loss on the surface around the rivet.

Another method of detecting surface corrosion is described in U.S. Pat. No. 5,491,409 to Flora et al. The Flora invention permits the detection of surface corrosion on metallic structures which are insulated by a coating or cover, or covered with marine growth. Excitation coils are wrapped around a magnetizing yoke which carries an alternating current in order to produce an alternating magnetic field by the magnetized yoke. The alternating magnetic fields induce an eddy current which runs through the metal component between the legs of a yoke and a pair of magnetic flux sensors are differentially connected beneath one or more of the excitation coils to sense a signal response. Thus, defects located on the surface can be detected. Nevertheless, Flora is only of interest and does not provide a method of quantifying the volume loss of these defects.

Moreover, the great majority of damage to structural members due to corrosion originates from corrosion damage within the fastener holes. However, none of the current inspection methods mentioned are applicable to evaluating corrosion damage in fastener holes.

SUMMARY OF THE INVENTION

The present invention provides a method for the direct measurement and quantification of the volume loss along the surface of a substrate and thus more accurately depicts the surface profile of a surface than conventional processes which can only provide comparative measurements of a surface profile or two dimensional anomalies on a test surface. In addition, the method of the invention can be used with various types of materials and can be used to measure volume losses even on non-planar surfaces such as around fasteners or inside fastener holes where corrosion defects often originate. The method of the invention allows a contour map of the surface of substrate to be produced illustrating the material lost due to corrosion or damage. Advantageously, the method of the invention allows for the early determination of metal loss due to corrosion and damage thereby allowing replacement or repair of the test substrate prior to failure of the substrate.

The method of the invention comprises inducing eddy currents in a test substrate, measuring the magnitude of the eddy current within the substrate at a plurality of locations on the surface of the test substrate, and converting the measured eddy current magnitudes at the locations to corresponding volume losses on the surface of the substrate using the eddy current magnitude measurements of a reference substrate having defects of predetermined volume loss. Typically, the measurements of the eddy current magnitude on the test surface are converted by multiplying a normalized eddy current magnitude for a sector on the surface of the test substrate both by a predetermined calibration factor ($C_f$) representing volume per unit area eddy current magnitude and the surface area of the sector to provide volumetric measurements of the metal loss in the sector. The calibration factor ($C_f$) is determined by measuring the magnitude of the eddy current produced for a plurality of defects having predetermined volume losses on the surface of a reference substrate.

In a specific method embodiment of the invention, the volume loss on the surface of a metal test substrate is measured by first calibrating the system using a reference substrate and then using the system to test the surface of a substrate. The system calibration comprises inducing an eddy current in a reference substrate having a surface comprising a plurality of sectors of predetermined surface area and predetermined volume loss such that at least a portion of the sectors have no volume loss and at least a portion of the sectors have a positive volume loss. The magnitude of the eddy current produced in the reference substrate is measured on the surface of the substrate at a plurality of locations within each sector and the eddy current magnitudes measured for the locations in the sectors having no volume loss are averaged to provide a threshold level (T). The threshold level (T) is then subtracted from the measured magnitudes for the locations in the sectors having positive volume loss to provide a normalized eddy current magnitude for each location. Preferably, the normalized eddy current magnitudes measured at each of the locations in the sector having the greatest volume loss are summed to provide a normalized eddy current magnitude for the sector of greatest volume loss. The predetermined volume of the sector of greatest volume loss is then divided by both the normalized eddy current magnitude for the sector of greatest volume loss and the surface area of the sector of greatest volume loss to produce a calibration factor ($C_f$) representing the measured volume per unit area eddy current magnitude.

Once the process is calibrated, a surface is tested by inducing eddy currents in the test substrate and measuring the magnitude of the eddy current produced within the substrate on the surface of the substrate at a plurality of locations within sectors of predetermined surface area. As in the calibration process, the locations of no volume loss are averaged to produce a threshold value ($T_{test}$). The measured eddy current magnitudes at the locations are decreased by the threshold value ($T_{test}$) to produce normalized eddy current magnitudes at the locations. The normalized eddy current magnitudes for the locations within each sector are summed to produce a normalized eddy current magnitude for each sector. Accordingly, the normalized eddy current magnitudes for each sector are multiplied by the calibration factor ($C_f$) and by the surface area of the sector to provide quantitive measurements of the volume loss for the sectors thereby providing a surface profile of volume loss on the test surface.

The present invention also includes a system for producing a surface profile of the volume loss along the surface of a metal substrate comprising means for inducing eddy currents in a test substrate, a measurement device for measuring the magnitude of the eddy current within the substrate at a plurality of locations on the surface of the substrate, and means for converting the measured magnitudes at the locations to corresponding volume losses on the test surface. Preferably, the inducing means and measurement device are an eddy current inspection probe having an inspection surface which corresponds to the test surface.

These and other features and advantages of the present invention will become more readily apparent to those skilled in the art upon consideration of the following detailed description which describes both the preferred and alternative embodiments of the present invention.

DETAILED DESCRIPTION OF THE INVENTION

The present invention will be described more fully hereinafter with reference to the accompanying drawings, in which preferred embodiments of the invention are shown. This invention can, however, be embodied in many different forms and should not be construed as limited to the embodiments set forth herein; rather, these embodiments are provided so that this disclosure will be thorough and complete, and will fully convey the scope of the invention to those skilled in the art.

The present invention is a method which can be used to quantify the volume loss at the various points on the surface of a substrate. Although the substrate is typically formed of metal and is described as a metal substrate herein, other substrate surfaces can also be tested according to the method described herein. In the method of the invention, the test system is first calibrated using a reference substrate and then a test substrate is tested according to the method of the invention using the data obtained from the calibration.

Figure 1:
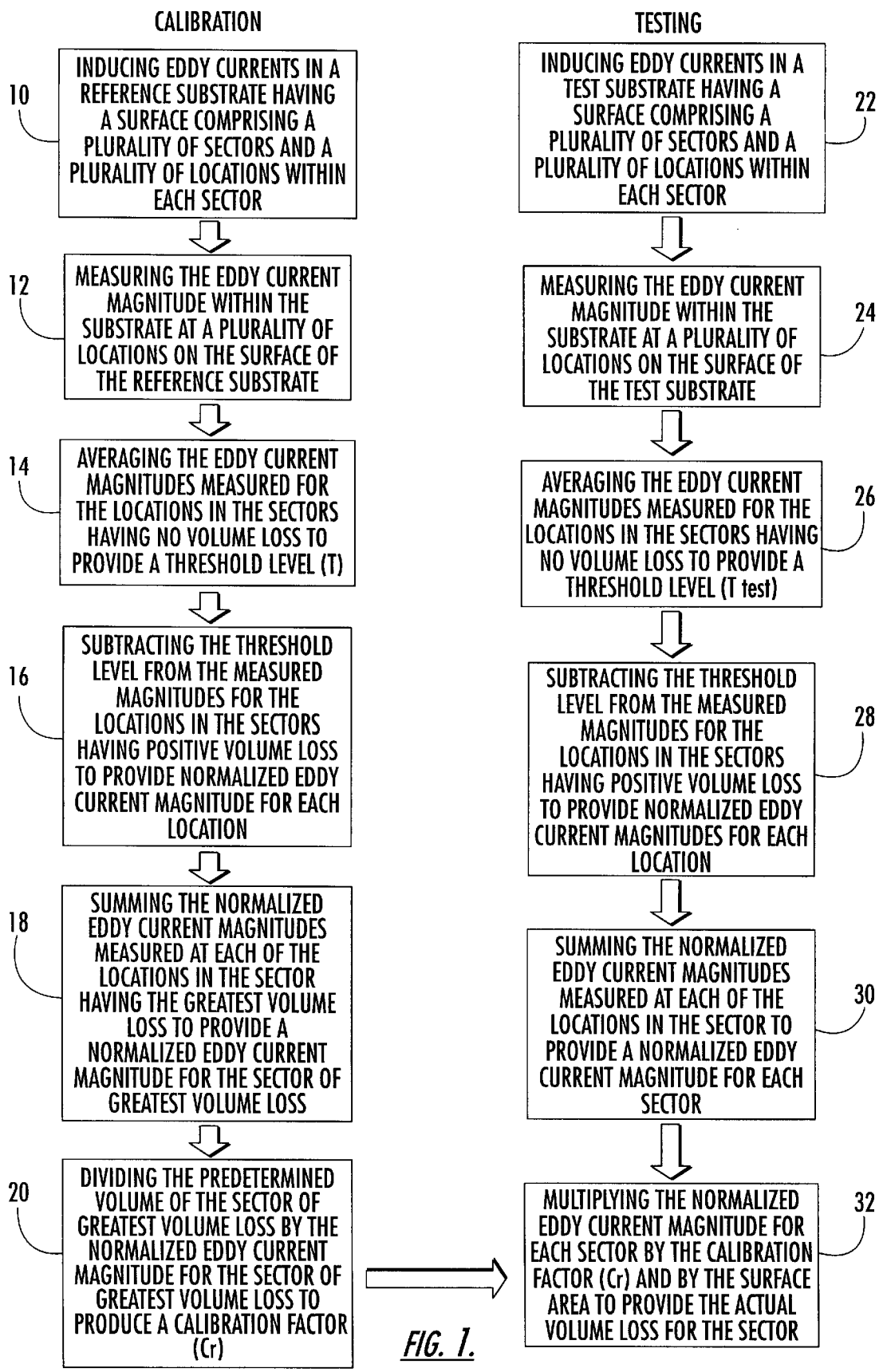
FIG. 1 is a flow chart illustrating calibration and test sequences of the invention.
Figure 2:
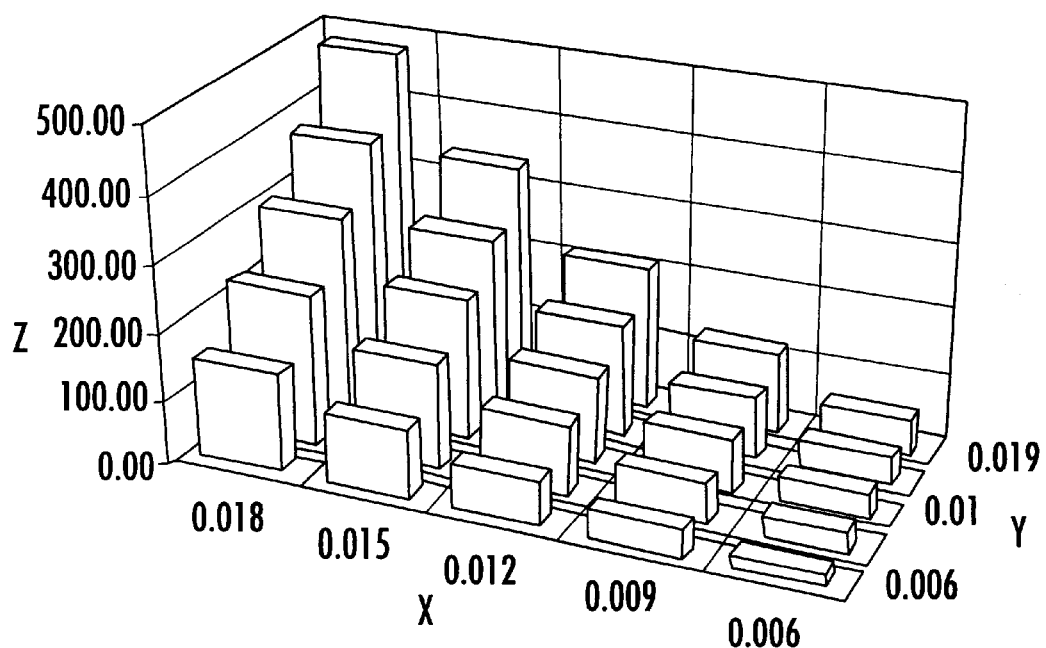
FIG. 2 is a three dimensional graph showing the calculated volumes of defects which simulate corrosion pitting in a reference standard.

The method of the invention is illustrated in FIG. 1. In the method of the invention, a reference substrate having surface defects of known volume is first selected having the same chemical composition and temper as the surface to be tested. For example, as shown in FIG. 2, the volumes for a series of surface defects are calculated for a reference substrate. The surface defects of the reference substrate are selected to resemble corrosion pitting and consist of a series of holes of varying depth in inches as illustrated along the X axis of FIG. 2 and of varying diameter as measured in inches along the Y axis of FIG. 2. The reference substrate is preferably divided into sectors of predetermined surface area with each sector containing no more than one defect. In FIG. 2, the calculated volumes for the defects in each sector appear along the Z axis and are plotted in cubic inches times $10^{6.}$ Additionally, the reference substrate typically has sectors of no volume loss to aid in the calibration of the system as described herein.

The reference substrate is first tested as designated at 10 in FIG. 1 by inducing eddy currents in the reference substrate. Preferably, the means for inducing eddy currents is an eddy current inspection probe 40 (FIG. 3), such as a DT20P Probe manufactured by Zetec Inc., which is also used to measure the eddy current responses produced as described in more detail below. The eddy current inspection probe 40 consists of a reference coil and a test coil. An AC current, such as a 200 kHz AC current, is passed through the coils to produce a primary electromagnetic field. The test coil is situated in proximity to the substrate such that the primary electromagnetic field generated by the test coil penetrates the substrate and induces eddy currents within the substrate. The magnitude of the eddy currents produced is directly proportional to the amount of metal that is present within the primary electromagnetic field and thus inversely proportional to the volume loss within this field. In other words, the larger the amount of metal in proximity to the primary field, the larger the eddy currents and thus the magnitude of the eddy current response. The eddy currents generate a second electromagnetic field which encompasses the test coil and has a either negating or complementary effect on the AC current flowing through the test coil. The eddy current response can be described as a "fill factor" or "lift off" which can be described as a percentage of the primary field that penetrates the metal sample such that a fill factor of 100% equates to no volume loss at the measured location. The resulting current flowing through the test coil can then be compared to the current in the reference coil to determine the eddy current response. As will be apparant to those skilled in the art, the current flowing through the reference coil is unaffected by the eddy currents such that the difference in the current flowing through the reference coil and the test coil provides a measure of the magnitude of the eddy currents and, in turn, a measure of the amount of metal that is present within the primary electromagnetic field.

The actual eddy current responses for a plurality of locations within each sector on the surface of the reference substrate are measured using a measurement device such as the eddy current inspection probe described above. Preferably, the eddy current inspection probe is designed to have a measurement surface corresponding to the surface of the reference substrate. For example, a probe having a circular measurement surface can be used to measure the eddy current responses produced in a connector hole. The eddy current inspection probe 40 can measure the actual eddy current response, but preferably measures difference between the eddy current magnitude of a reference coil equating to a fill factor of 100% and the eddy current magnitude of a test coil relating to the actual eddy current magnitude at a location, as described above.

The eddy current response is typically measured at a plurality of locations at regular intervals along the x-axis and y-axis of the surface such that each sector on the surface of the reference substrate contains the same number of measurements. The measurements of the eddy current magnitudes in the sectors containing no flaws or defects (i.e. no volume loss) are averaged for each of the locations to provide a threshold or background noise level (T) designated at 14. This value becomes the offset value to normalize the remaining data to a zero baseline. The threshold level (T) is then subtracted from each of the measurements in the sectors containing defects or flaws to normalize the eddy current magnitudes for the locations within these sectors as designated at 16.

The normalized eddy current magnitudes are then summed for each of the locations within each sector to produce a normalized eddy current for the sector as designated at 18.

Figure 4:
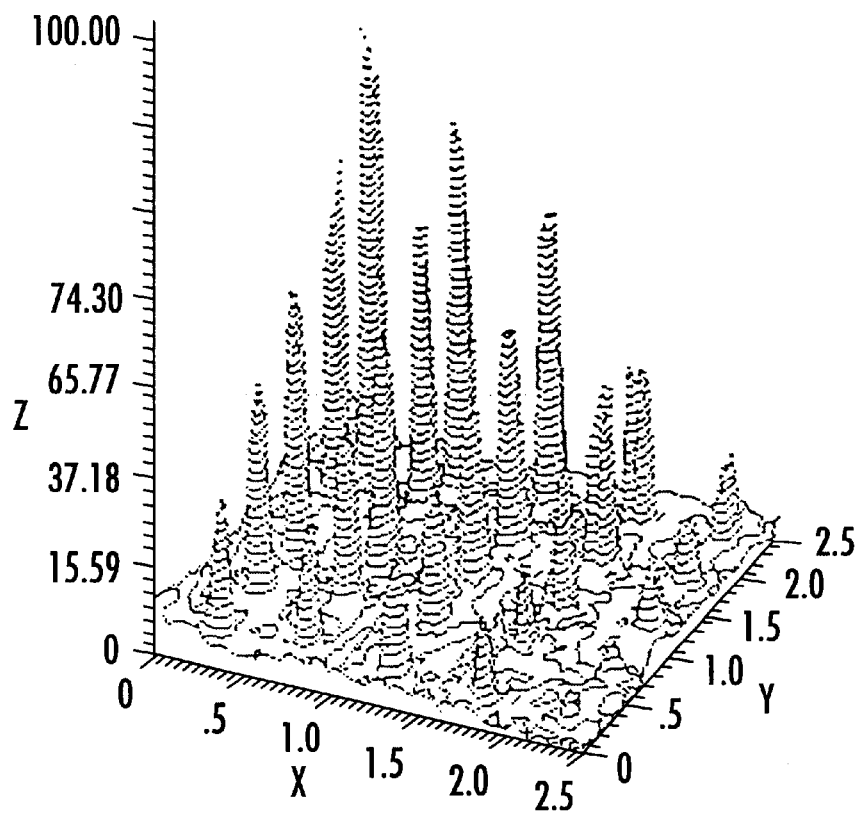
FIG. 4 illustrates the actual eddy current response obtained from the reference volumes shown in FIG. 2.
Figure 3:
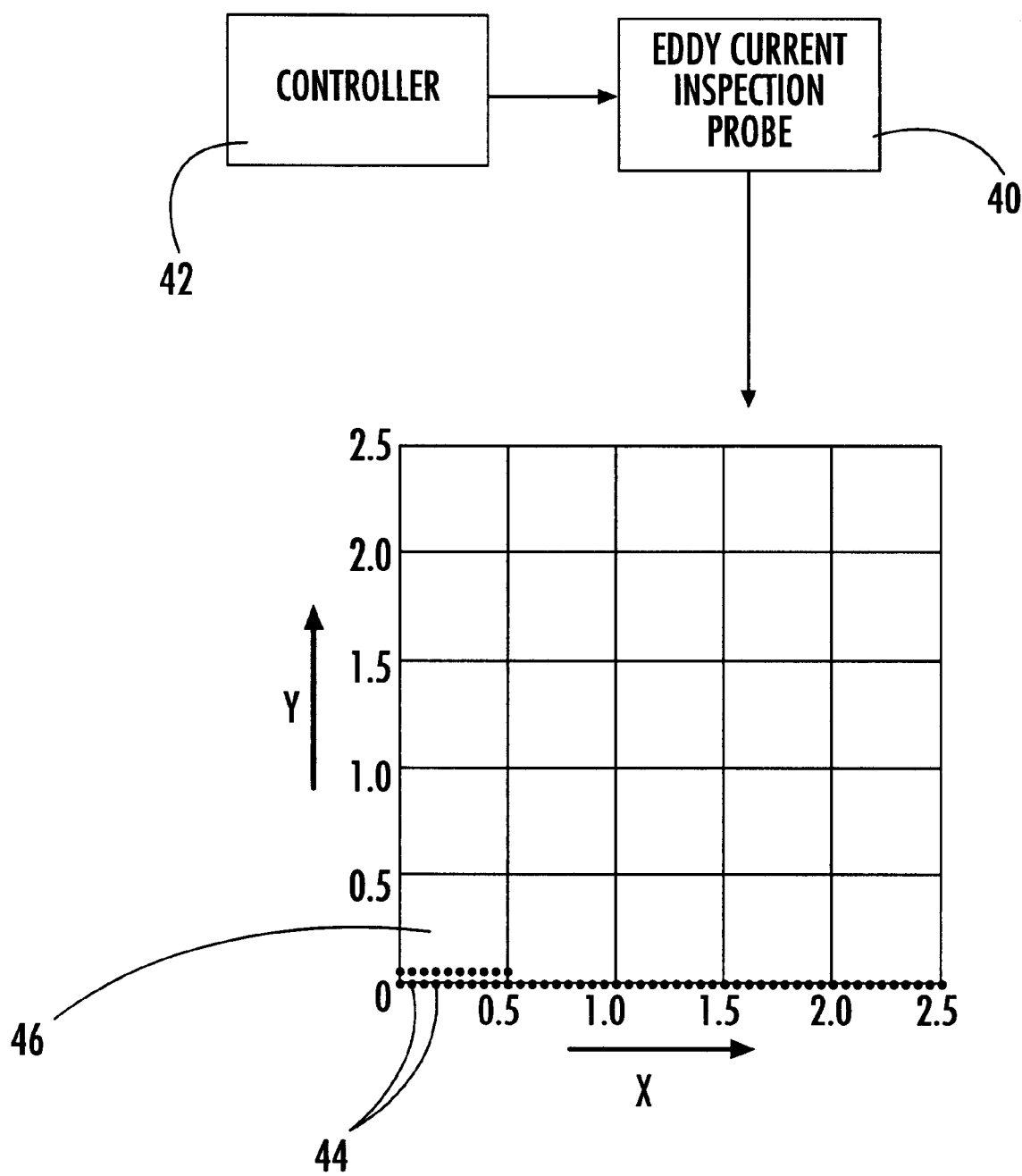
FIG. 3 is a schematic drawing of the volume measurement system used in accordance with the invention.

For purposes of illustration, FIGS. 3 and 4 illustrate a 2.5 inch×2.5 inch scan area for the scanning of a reference surface having positive volume losses as measured in FIG. 2. In order to produce the contour scan or C-Scan illustrated in FIG. 4 of the reference substrate of FIG. 2, a controller 42 controls the measurement device which scans the reference surface in the X direction and samples eddy current values at locations 44 every $50/1000$th of an inch. When the end of the sample area was reached, the measurement device is moved $50/1000$th of an inch in the Y direction and again moves across the surface in the X direction. This scanning process is repeated until the magnitudes of the eddy current responses across the entire scan area have been measured. Although the test area was scanned in this manner, other scan methods such as helical or raster scans can be used as long as the entire test area is scanned. The eddy current magnitudes for each sector 46 were then measured by summing the normalized measurements for each location in the sector (18 in FIG. 1) and the resulting eddy current response for each sector was graphed in FIG. 4. The Z direction of FIG. 4 relates to percent of total scale wherein 100% relates to the sector having greatest volume loss.

The values in FIG. 4 can then be used to relate the predetermined volumes and predetermined surface areas for the sectors to the normalized magnitudes of the eddy current for the sectors. A preferred method of providing this relationship is to use the measurements for the sector having the greatest volume loss. The predetermined volume for the sector of greatest volume loss is divided by the normalized eddy current response for the sector and the surface area of the sector to produce a calibration factor ($C_f$) representing the volume per unit area eddy response 20. The calibration factor ($C_f$) can then be used for testing other surfaces. Although this is the preferred method of calibration, one or more of the sectors can be used as described above to produce the calibration factor ($C_f$).

Once the system is calibrated, eddy currents are induced in a test surface in the same manner described in the calibration as designated at 22. The magnitude of the eddy current response produced in the test substrate is then measured along the test surface at a plurality of locations at regular intervals using a measurement device having a measurement area corresponding to the test surface as designated at 24. In order to provide accurate volumetric measurements, the intervals at which the eddy current magnitudes are measured are the same as those used in the calibration. A threshold value ($T_{test}$) is then determined for the test substrate as designated at 26 by averaging the eddy current responses for the locations of no volume loss. The eddy current magnitudes at each location are then normalized by substraction, the threshold value $T_{(test)}$ as designated at 28. The test surface is divided into sectors of predetermined surface area and the normalized eddy current magnitudes for the locations within each sector are summed to provide the normalized eddy current response for the sector as designated at 30. The normalized eddy current response and the surface area are then multiplied by the calibration factor ($C_f$) to produce the actual volume loss within the sector in cubic inches as designated at 32. The volume loss measurements on the test surface are determined using suitable converting means (such as a microprocessor) and can then be graphed to produce a contour map or C-scan of the test surface. The C-scan provides a true quantitative measurement of the volume loss due to corrosion or damage on the test surface and allows actual volume of the metal loss for each sector expressed in cubic inches.

Correlation between the fill factor and the amount of metal loss due to the corrosion damage in the sample permits the direct measurement and quantification of the amount of metal loss due to the corrosion activity. By properly calibrating the eddy current response to known volumes from reference standards, the metal loss resulting from corrosion damage detected can be quantified accurately. Once metal loss is detected and the amount of the loss is accurately quantified, a determination of a course of action for the test part such as replacement or repair of the part can be determined.

The present invention provides a method for the direct measurement and quantification of the material volume loss along the surface of a substrate and thus more accurately depicts the surface profile of a surface than conventional processes which can only provide comparative measurements of a surface profile. The method of the invention thus allows a contour map of the surface of substrate to be determined illustrating the material lost due to corrosion, damage or other processes. Advantageously, the method of the invention allows for the early determination of metal loss due to corrosion and damage thereby allowing replacement or repair of the test substrate prior to failure of the substrate. The method of the invention can be used with various types of materials and can be used to measure volume losses even on indentations and projections such as around rivets and other connectors. In addition, historical data can be collected for specific test articles and other reports generated such as future test schedules, statistical error data regarding failed articles which may be associated with specific regions in the X-Y plane of the test article such as aircraft wings and control surfaces. The method of the invention also permits the collection of historical data which allows the establishment of test schedules for various types of vehicles.

Many modifications and other embodiments of the invention will come to the mind of one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for measuring the volume loss of a metal substrate comprising the steps of:
   inducing eddy currents in a test substrate;
   measuring the magnitude of the eddy current produced within the substrate at a plurality of locations on the surface of the substrate; and
   converting the measured eddy current magnitudes at each location to corresponding volume losses at each location on the surface of the test substrate using the eddy current magnitude measurements of a reference substrate having defects of predetermined volume loss.

2. A method for measuring the volume loss of a metal substrate comprising the steps of:
   inducing eddy currents in a test substrate;
   measuring the magnitude of the eddy current produced within the substrate at a plurality of locations on the surface of the substrate; and
   converting the measured eddy current magnitudes at each location to corresponding volume losses on the surface of the test substrate by multiplying the measured eddy current magnitude for a sector on the surface of a test substrate by a predetermined calibration factor ($C_f$) representing volume per unit area eddy current magnitude and by the surface area of the sector to provide measurements of the volume loss within the sector.

3. The method according to claim 2 wherein the eddy current magnitude for the sector is the sum of the eddy current magnitudes of the locations located within the sector.

4. A method for measuring the volume loss of a metal substrate comprising the steps of:
   inducing eddy currents in a reference substrate;
   measuring the magnitude of the eddy current produced within the substrate at a plurality of locations of known volume loss on the surface of the substrate;
   determining a calibration factor ($C_f$) based on the measured magnitudes at the locations on the reference substrates;
   inducing eddy currents in a test substrate;
   measuring the magnitude of the eddy current produced within the substrate at a plurality of locations on the surface of the substrate; and
   converting the measured eddy current magnitudes at each location to corresponding volume losses on the surface of the test substrate using the calibration factor ($C_f$).

5. The method according to claim 4 wherein the step of determining the calibration factor ($C_f$) comprises selecting a sector of predetermined volume loss and surface area, summing the eddy current measurements for the locations within the sector, to provide an eddy current magnitude for the sector and dividing the predetermined volume loss of the sector by the eddy current magnitude for the sector and the surface area of the sector to produce calibration factor ($C_f$).

6. A method for measuring the volume loss of a metal substrate comprising the steps of:
   inducing eddy currents in a reference substrate having a surface comprising a plurality of sectors of predetermined surface area and predetermined volume loss such that at least a portion of the sectors have no volume loss and at least a portion of the sectors have a positive volume loss;
   measuring the magnitude of the eddy current produced within the reference substrate at a plurality of locations within each sector;
   averaging the eddy current magnitudes measured for the locations having no volume loss to provide a threshold level (T);
   normalizing the eddy current magnitudes for the locations in the sectors having positive volume loss by subtracting the threshold level (T) from the measured magnitudes at the locations;
   summing the normalized eddy current magnitudes measured at each of the locations in a sector to provide a normalized eddy current magnitude for the sector;
   determining a calibration factor ($C_f$) representing the measured volume per unit area eddy current magnitude by dividing the predetermined volume loss of the sector by the normalized eddy current magnitude for the sector and the surface area of the sector;
   inducing eddy currents in a test substrate;
   measuring the magnitude of the eddy current produced within the substrate at a plurality of locations on the surface of the substrate; and
   converting the measured eddy current magnitudes at each location to corresponding volume losses on the surface of the test substrate using the calibration factor ($C_f$).

7. A process for measuring the volume loss of a metal substrate comprising the steps of:
   inducing eddy currents in a metal reference substrate having a surface comprising a plurality of sectors of predetermined surface area and predetermined volume loss such that at least a portion of the sectors have no volume loss and at least a portion of the sectors have a positive volume loss;
   measuring the magnitude of the eddy current produced within the reference substrate at a plurality of locations within each sector;
   averaging the eddy current magnitudes measured for the locations in the sectors having no volume loss to provide a threshold level (T);
   subtracting the threshold level (T) from the measured magnitudes for the locations in the sectors having positive volume loss to provide a normalized eddy current magnitude for each location;
   summing the normalized eddy current magnitudes measured at each of the locations in the sector having the greatest volume loss to provide a normalized eddy current magnitude for the sector of greatest volume loss;
   dividing the predetermined volume of the sector of greatest volume loss by the normalized eddy current magnitude for the sector of greatest volume loss and the surface area of the sector of greatest volume loss to produce a calibration factor ($C_f$) representing the measured volume per unit area eddy current magnitude;

inducing eddy currents in a metal test substrate;

measuring the magnitude of the eddy current produced within the test substrate at a plurality of locations on the surface of the substrate and within sectors of predetermined surface area;

subtracting the measured eddy current magnitudes at the locations by the threshold value (T) to produce normalized eddy current magnitudes at the locations;

summing the normalized eddy current magnitudes for the locations within each sector to produce a normalized eddy current magnitude for each sector;

multiplying the normalized eddy current magnitudes for each sector by the calibration factor ($C_f$) and by the surface area of the sector to provide volumetric measurements of the volume loss at the locations thereby providing a surface profile of volume loss on the test surface.

8. A system for producing a profile of the volume loss along the surface of a metal substrate comprising:

means for inducing eddy currents in a test substrate;

a measurement device for measuring the magnitude of the eddy current produced within the substrate at a plurality of locations on the surface of the substrate; and means for converting the measured magnitudes at the locations to corresponding volume losses at each location on the surface.

9. The system according to claim 8 wherein said measurement device is an eddy current inspection probe having an inspection surface which corresponds to the test surface.

10. The system according to claim 8 wherein said inducing means comprises means for generating a primary magnetic field in the test substrate.

11. A system for producing a profile of the volume loss along the surface of a metal substrate comprising:

means for inducing eddy currents in a test substrate, said test substrate having a surface comprising sectors of predetermined surface area;

a measurement device for measuring the magnitude of the eddy current produced within the substrate at a plurality of locations on the surface of the substrate; and means for converting the measured magnitudes at the locations to corresponding volume losses on the surface, said converting means comprising:

means for normalizing the eddy current magnitudes measured on the surface of the substrate, means for summing the normalized eddy current magnitudes within a sector to provide a normalized eddy current magnitude for the sector, and means for multiplying the normalized eddy current magnitude of the sector by the surface area of the sector and a calibration factor ($C_f$) representing the volume per unit area eddy current magnitude to calculate the actual volume loss on the surface of the substrate within each sector.

* * * * *